United States Patent

Yerfino et al.

[11] Patent Number: 5,968,016
[45] Date of Patent: Oct. 19, 1999

[54] RETRACTABLE HYPODERMIC NEEDLE FOR DISPOSABLE TUBING GUIDE

[76] Inventors: Daniel Alberto Yerfino, Esquiú 863, (7600), Mar del Plata; Aldo Luis Ducler, Corrientes 415, 6° Floor, Buenos Aires, both of Argentina

[21] Appl. No.: 09/149,762

[22] Filed: Sep. 9, 1998

[30] Foreign Application Priority Data

Jun. 30, 1998 [AR] Argentina ............... P 98 01 03163

[51] Int. Cl.⁶ ............................................ A61M 5/00
[52] U.S. Cl. ..................... 604/177; 604/192; 604/198
[58] Field of Search ............................. 604/177, 195, 604/192, 198, 110, 187

[56] References Cited

U.S. PATENT DOCUMENTS

| | | |
|---|---|---|
| 5,320,606 | 6/1994 | Jore . |
| 5,350,368 | 9/1994 | Shields . |
| 5,549,571 | 8/1996 | Sak . |
| 5,656,031 | 8/1997 | Thorne et al. . |

*Primary Examiner*—John D. Yasko
*Attorney, Agent, or Firm*—Finnegan, Henderson, Farabow, Garrett & Dunner, L.L.P.

[57] ABSTRACT

A retractable hypodermic needle for a disposable tubing guide including a cylindrical coupling having proximal end, for connection to the disposable tubing guide, and a flexible distal end portion having opposite internal protrusions. A penetrating tube emerges from the distal end of the cylindrical coupling and has a tube duct opening through a tube base having an external transverse catch initially secured by the opposite internal protrusions at the distal end portion of the cylindrical coupling. A tensioned elastic tube, having a distal end connected in fluid communication with the penetrating tube duct and a proximal end connected in fluid communication with the disposable tubing guide, provides a retraction device ro the penetrating tube when a pair of diametrically opposite exterior gripping tabs on the flexible distal end of the cylindrical coupling and in coincidence with the internal annular protrusions of the tubular coupling are pulled apart.

6 Claims, 3 Drawing Sheets

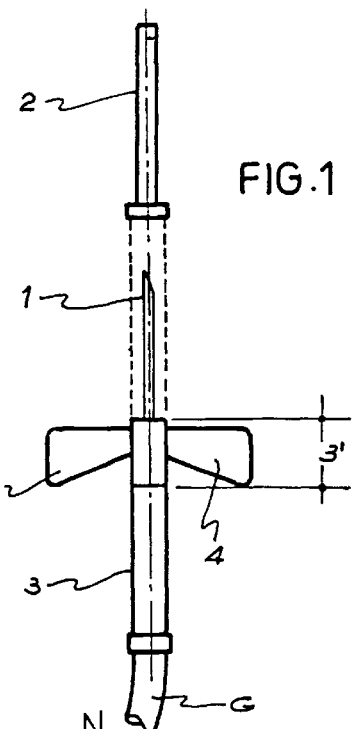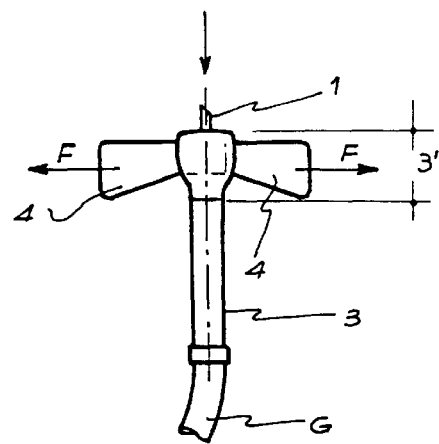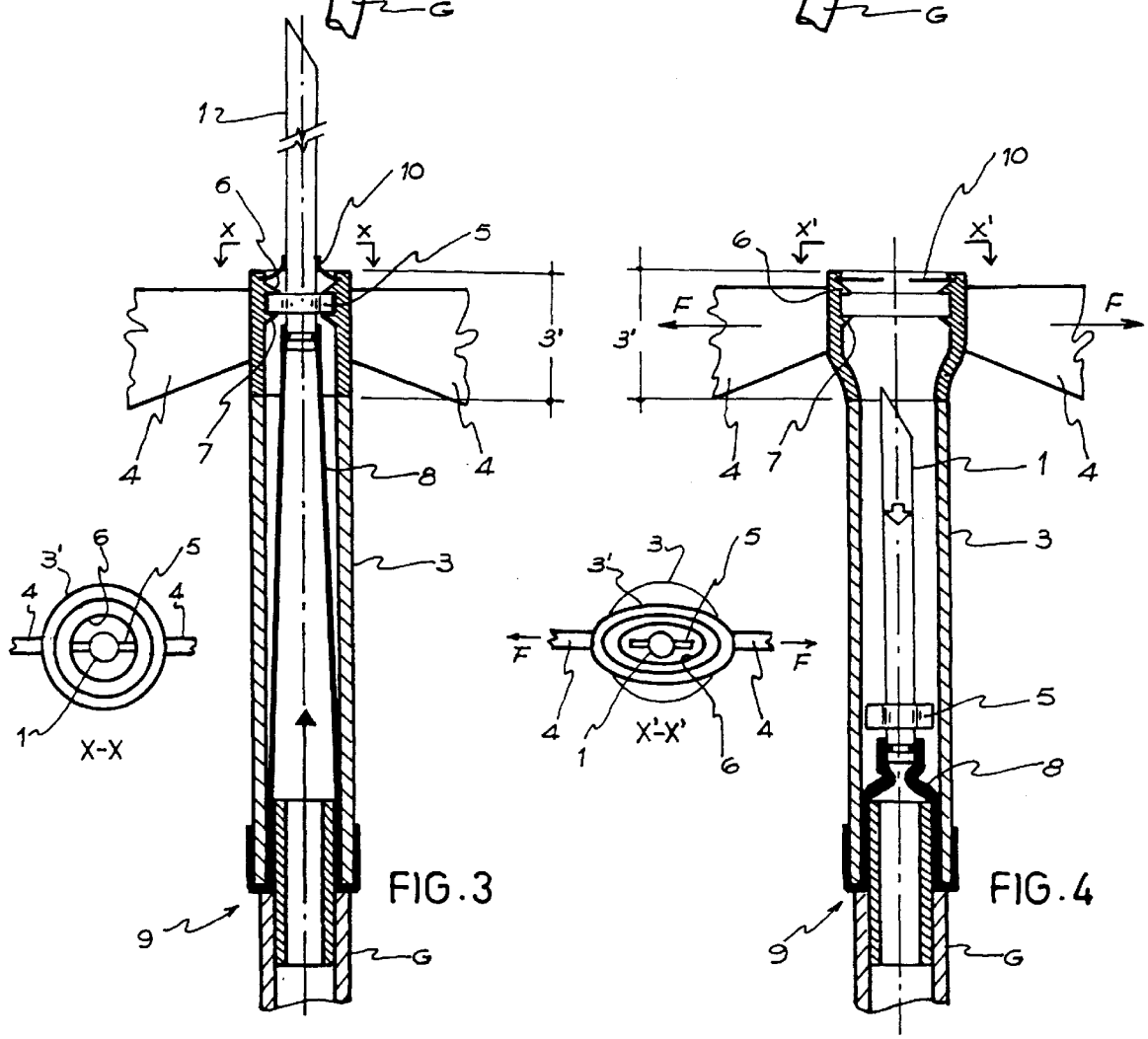

RETRACTABLE HYPODERMIC NEEDLE FOR DISPOSABLE TUBING GUIDE

The present application for a Patent of Invention relates to a RETRACTABLE HYPODERMIC NEEDLE FOR A DISPOSABLE TUBING GUIDE, of the type used in blood transfusions and the administering of serum or medications as a drip, in human and veterinary medicine.

Taken as a whole, it deals with a needle provided with a guide coupling with grips formed as transverse tabs, which, when tensile forces are exerted in opposite directions, deform the hollow cylindrical core with which they are integral at its flexible end, releasing an internal latching means fixed to the base of the needle, leaving the latter exposed to the retracting action of an elastic means, which is initially tensioned and which, since it is integral with the needle, causes it to move backward instantaneously so as to become housed entirely in a segment behind the abovementioned latching region, this segment being rigid, said elastic means being tubular, with its duct axially coincident with that of the needle, so that it forms part of the flow line.

Hypodermic needles for such purposes are known, these having a grip with a guide coupling at their base, and being morphologically similar to the one described; they are known as "Butterfly" needles, but they differ in their functional aspect in that they lack the retracting action.

Moreover, with reference to disposable safety syringes with a retracting needle, the use of tubular elastic means is known, such as those applied to the U.S. Pat. Nos. 5,320,606 and 5,656,031, without these constituting precedents standing in the way of this presentation, as they have different uses and completely different latching and triggering means.

Closer to the topic in which we are interested, the U.S. Pat. No. 5,549,571 is presented, which claims a needle protector for a perfusion guide, which shoots outwards, that is to say from the coupling toward the pointed end of the needle, by the action of an elastic means acting by expansion, leaving part of its tube uncovered and requiring a release trigger in a position close to the line of retraction, which complicates its actuation, creating the risk of hand contact with the needle during its abrupt movement, and the U.S. Pat. No. 5,350,368, even more complex, whose trigger means is defined by the expansion of a longitudinally divided nozzle, which fits tightly around a swelling of the retracting assembly, a clip having to be withdrawn in order to release it.

The abovementioned accounts, and the one corresponding to this presentation, are aimed at finding a solution to the risk which is frequently run by medical and auxiliary personnel at the instant when the corresponding tubing guide is disconnected from the patient, the hypodermic needle being extracted from his body. In these circumstances, the needle, which is of light weight and small dimensions, remains coupled to the end of the flexible tube, acquiring a mobility which is difficult to control, as a consequence of its length, a slight rigidity (memory) tending to maintain a sinuous and helical profile, acquired while in use or in its packaging and capable of causing infecting punctures.

This patent provides a highly effective solution to the drawbacks set out, with a tubular coupling provided, at its distal end with respect to its junction with the flexible tube duct (guide), with a flexible segment with two annular protrusions on its inner face, coinciding in position with two tabs projecting diametrically from its outer face. Said segment houses within it the proximal end of a hypodermic needle, integral with a transverse catch, which, in its initial presentation, holds it in the extended position, retained by the latch of said transverse catch between the abovementioned annular protrusions. At its proximal end, the needle is axially integral with an elastic tube which, in the position described, exerts a tensile force toward its opposite end, at which it is integral with the end at which the coupling is joined to the guide.

In the manner described, once the packaging has been opened, the protective sheath is removed from the needle so that it can be inserted under the skin, opening the way for the inoculation or extraction; with this operation completed, the practitioner will take one of the grips between the thumb and index finger of each hand, causing a slight tension in opposite directions, in such a way that a deformation occurs due to the flexibility of the circular section of the coupling in the region adjacent to the latch, causing the triggering of the transverse catch integral with the tube of the needle, which catch was retained between the internal annular protrusions, the needle thereby becoming exposed to the retracting force exerted by the elastic tube, which has one end connected to its base and the other to the guide junction, until it becomes housed in the protective segment, with rigid, rear catch in said junction region, being prevented from causing accidents, so that the doctor or medical auxiliary can carry on with the appropriate tasks, free from concerns about such an eventuality.

Additionally, the tube of the coupling will be equipped with a membrane close to its distal nozzle, in order to prevent liquids flowing back when the needle is retracted.

Another alternative envisaged for this purpose consists in providing the needles referred to with their elastic tube in torsion and the tube which houses it equipped with longitudinal guides so that said torsion is maintained during retraction. In this way, the helically arranged elastic fibers, at the moment when they contract, cause the elastic tube to become constricted, preventing liquid escaping.

A third option, to the same end, is given by a reduction of the internal section of the coupling, in its proximal region, which constricts the duct of the elastic tube when, axially contracted, it increases the thickness of its wall.

As an additional advantage, the gripping tabs can each be provided individually with adhesive strips which run along their length, in order to allow them to be fixed to the patient's body, immobilizing the needle once it has been inserted. In this case, the extending, adhesive surfaces will initially be covered by protective strips which can easily be removed.

In order to give concrete form to the advantages thus briefly outlined, and in order to facilitate an understanding of the constructional and functional characteristics of the RETRACTABLE HYPODERMIC NEEDLE FOR A DISPOSABLE TUBING GUIDE of the invention, a preferred exemplary embodiment and variants are described below, which are illustrated diagrammatically, but to no particular scale, in the attached sheets of drawings, with the express statement that, precisely because an example is involved, no corresponding limiting or exclusive character should be assigned, but that it simply serves merely to illustrate the basic design on which it is founded.

FIG. 1 is a view of the needle in its initial position with respect to the coupling, with the protective sheath removed.

FIG. 2 is a view equivalent to the previous one, with the needle in the initial position.

FIG. 3 is a section, through a diametral plane, of the needle in the initial position.

FIG. 4 is a section equivalent to the previous one, with the needle retracted.

Figure 6:
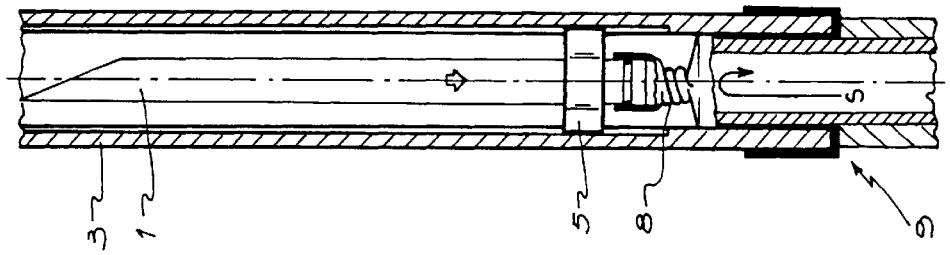

FIG. 6, in a section equivalent to the previous one, shows the needle retracted and the duct constricted.

Figure 7:
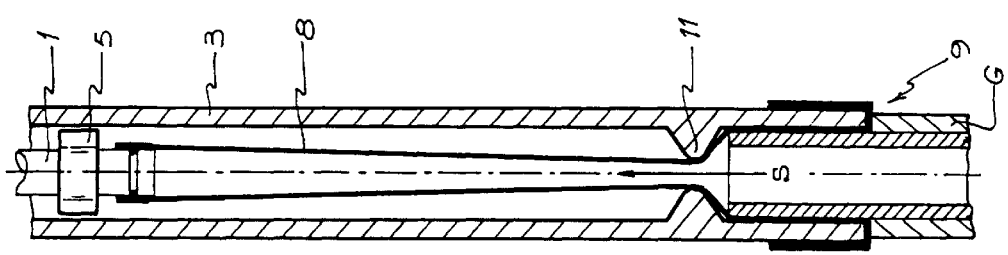

FIG. 7, in a section similar to the two previous ones, shows a needle beginning to be retracted, according to the option of constricting by swelling of the elastic wall.

Figure 8:
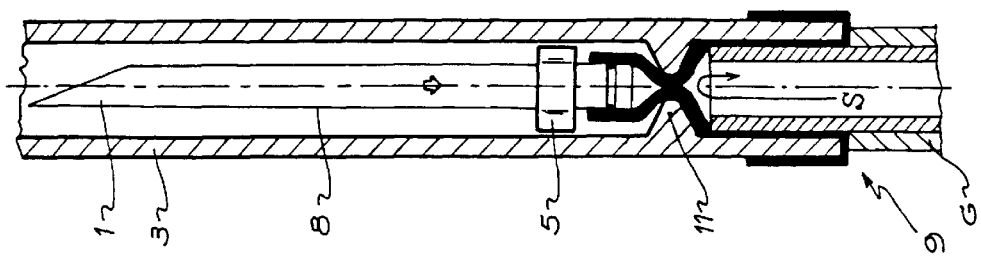

FIG. 8 is an illustration equivalent to the previous one, with the needle retracted and the elastic tube closed off.

Figure 9:
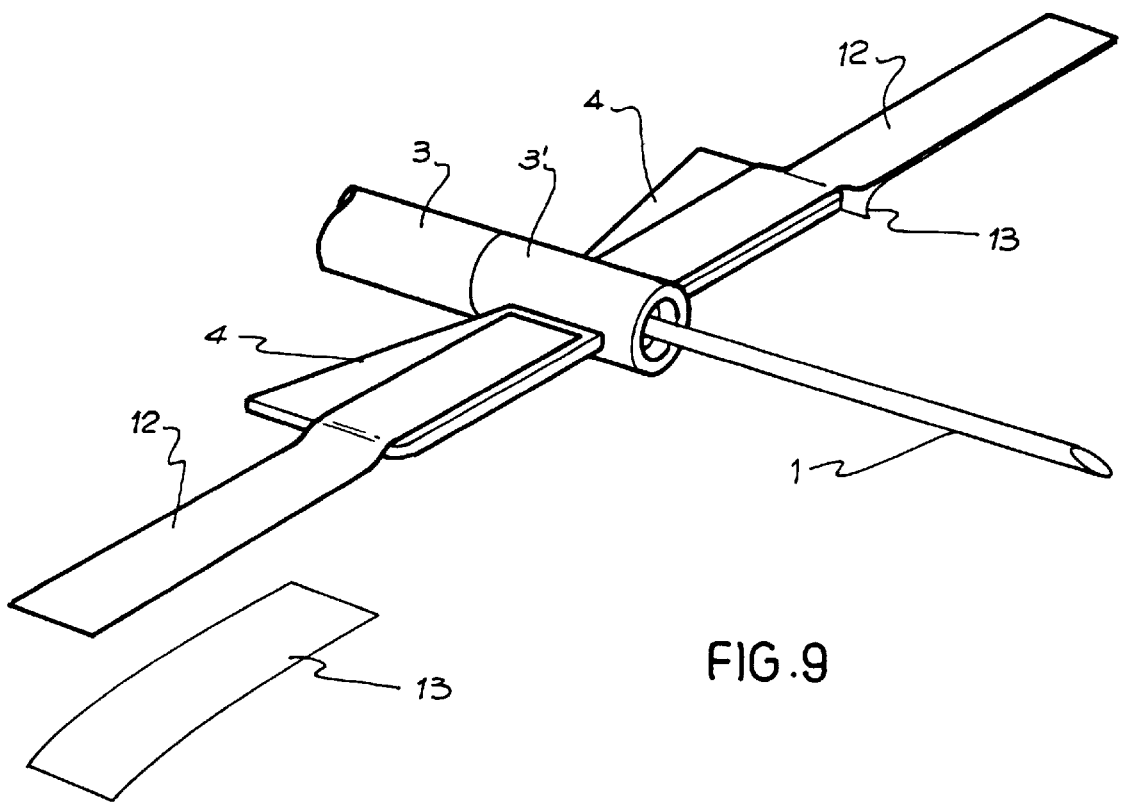

FIG. 9 is a view in perspective of a needle like the one invented, provided with adhesive fixing strips.

As can be seen in FIG. 1, the needle invented consists of a penetrating tube -1-, initially protected by the sheath -2-, which emerges from a coupling -3- fixed to the guide -G-, said coupling being fitted with the tab grips -4- in its flexible segment -3'-.

In FIG. 2, the penetrating tube -1- is almost completely retracted, as a consequence of the deformation of the segment -3'-, the mechanics of which are illustrated in successive figures, under the slight force exerted on the grips -4-, in the direction indicated by the arrows -F-; this action is performed by the operator when extracting the needle from the patient, in order to dispose of it.

FIGS. 3 and 4 sequentially show the operation of the invented needle; in the first of them, the penetrating tube -1- is exposed, in a position determined by the retention of the flat, transverse catch -5- between the annular protrusions -6- and -7- of the coupling tube -3- in its flexible segment -3'-, resisting the tensile force exerted by the elastic tube -8-, integral at one end with said penetrating tube and at the other with the region of the junction -8- with the guide -G-; in the second sequence, the gripping tabs have been forced in the directions -F-, and the section of the coupling tube included between them has undergone a widening, given its flexibility, which allows the transverse catch -5- to be released from the annular protrusion -7-, the penetrating tube -1- being retracted to the position illustrated, by the contraction of the elastic tube -8-. In this basic option, the distal end of the coupling tube has an inner membrane -10, which shuts off the duct when the penetrating tube moves back, and the segment -3'- resumes its original shape, preventing residual leakage.

Figure 5:
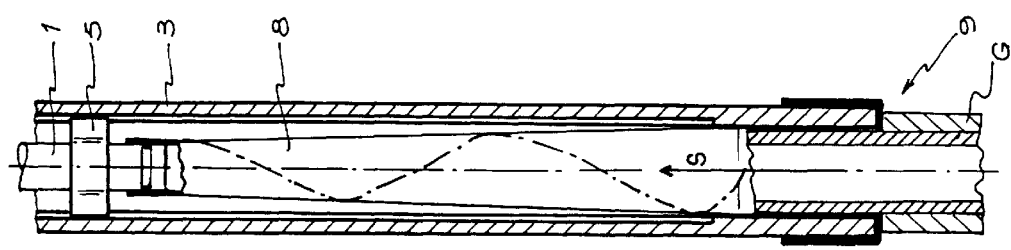
FIG. 5 is a section through a diametral plane, of a segment of the coupling with the needle beginning its retracting travel, in order to show the proposed variant for closing off the elastic tube by torsion.

In FIGS. 5 and 6 is shown, diagrammatically, the alternative way of closing off the elastic tube -8- by torsion, the tube, as can be seen in FIG. 5, having its elastic fibers oriented helically as the lines of dots and dashes show, without impeding the flow of blood or medication solution in the direction -S-; while in the retracted position, shown by FIG. 6, the contraction of the helically arranged fibers, added to the swelling of the elastic walls, cause the elastic tube to be constricted, which prevents the passage of liquid.

Finally, FIGS. 7 and 8 are representative of another alternative option for closing off, when the needle is protected, out of action. This option is based on the fact that a reduction in the section -11- of the coupling tube will not succeed in blocking the passage -S- when the elastic tube -8- is under tension (FIG. 7), but when the tube contracts (FIG. 8) its walls thicken considerably and said thickness doubles, within the reduced section -11-, and causes a constriction which closes it off.

In FIG. 9, the gripping tabs -4- both have adhesive strips -12-, on their faces corresponding to the same plane, which strips are fixed to the patient's skin by the adhesive, inside faces of their excess lengths, so immobilizing the needle, with its penetrating tube already inserted. The protective strips -13-, provided initially, are removed by said operation, as illustrated on one of them.

The Retractable Hypodermic Needle for a Disposable Tubing Guide, as described, is comprised within the scope of the protection defined, in its fundamental aspect, by the clauses of the claims which follow.

We claim:

1. A retractable hypodermic needle for a disposable tubing guide, comprising:

a cylindrical coupling having proximal end for connection to the disposable tubing guide, and a flexible distal end portion having opposite internal protrusions;

a penetrating tube emerging from the distal end of the cylindrical coupling and having a tube duct opening through a tube base having an external transverse catch initially secured by the opposite internal protrusions at the distal end portion of the cylindrical coupling, the cylindrical coupling having a length behind the flexible distal end portion and the internal protrusions, larger than the length of the penetrating tube;

a tensioned elastic tube having a distal end connected in fluid communication with the penetrating tube duct and a proximal end connected in fluid communication with the disposable tubing guide; and a pair of diametrically opposite exterior gripping tabs on the flexible distal end of the cylindrical coupling and in coincidence with the internal annular protrusions of the tubular coupling, whereby the external transverse catch is released from the internal protrusions upon pulling the gripping tabs in opposite directions.

2. The retractable hypodermic needle of claim 1 including a transverse elastic membrane in the distal end portion of the cylindrical coupling to operate in the manner of a diaphragm valve.

3. The retractable hypodermic needle of claim 1, wherein the tensioned elastic tube is installed in torsion, and including longitudinal guide tracks on an inner wall of the cylindrical coupling to guide the transverse catch along a retraction path.

4. The retractable hypodermic needle of claim 1, wherein the tensioned elastic tube passes through a restriction in the cylindrical coupling near the proximal end thereof to provide an internal section at the restriction of a diameter less than twice the thickness of the wall of the elastic tube in a relaxed state.

5. The retractable hypodermic needle of any one of claims 1 to 4, including adhesive strips extending beyond the gripping tabs in a diametrical direction, and protective strips initially covering the adhesive strips.

6. The retractable hypodermic needle of claim 5, wherein the tensioned elastic tube is made of latex.

* * * * *